(12) United States Patent
Chai et al.

(10) Patent No.: US 6,686,503 B2
(45) Date of Patent: Feb. 3, 2004

(54) METHODS FOR THE SYNTHESIS OF HIGHLY SUBSTITUTED 2,4-DIOXOPIPERIDINE LIBRARIES

(75) Inventors: Wenying Chai, San Diego, CA (US); William V. Murray, Belle Mead, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 163 days.

(21) Appl. No.: 09/880,623

(22) Filed: Jun. 13, 2001

(65) Prior Publication Data

US 2001/0041345 A1 Nov. 15, 2001

Related U.S. Application Data

(62) Division of application No. 09/546,793, filed on Apr. 11, 2000, now Pat. No. 6,288,235.
(60) Provisional application No. 60/129,211, filed on Apr. 14, 1999.
(51) Int. Cl.$^7$ ............... C07C 239/00; C07C 233/00; C07D 211/04; C07D 211/86
(52) U.S. Cl. ............. 564/155; 435/7.1; 435/DIG. 40; 435/DIG. 49; 546/192; 546/194; 546/245; 546/279.7; 546/281.7; 546/185; 564/152; 564/169; 564/193; 564/194; 564/199; 564/200
(58) Field of Search ............... 435/DIG. 40, DIG. 49, 435/7.1; 546/192, 194, 245, 279.7, 281.7, 185; 564/152, 155, 169, 193, 194, 199, 200

(56) References Cited

FOREIGN PATENT DOCUMENTS

| EP | 0149534 A2 | 7/1985 |
| WO | 95/14012 A1 | 5/1995 |

OTHER PUBLICATIONS

Wenying Chai et al., Solid phase synthesis of highly substituted 2,4–dioxopiperidines, Tetrahedron Letters 40(1999) pp. 7185–7188.
Caplus DN 132:12251,Wenying Chai et al., English Abstract, Vol 40 Issue 40. 1999.

*Primary Examiner*—Maurie Garcia Baker

(57) ABSTRACT

The invention relates to methods of synthesizing libraries of diverse and complex highly substituted 2,4-dioxopiperidine compounds of the general formula:

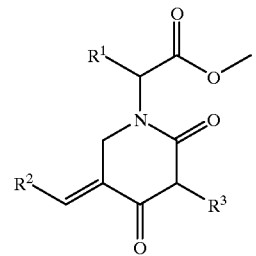

wherein $R^1$, $R^2$ and $R^3$ are as herein described, novel intermediates useful for synthesizing such 2,4-dioxopiperidine compounds and methods for identifying and isolating the compounds.

12 Claims, No Drawings

METHODS FOR THE SYNTHESIS OF HIGHLY SUBSTITUTED 2,4-DIOXOPIPERIDINE LIBRARIES

CROSS-REFERENCE TO RELATED APPLICATIONS

This application is a division and claims the benefit of U.S. Ser. No. 09/546,793 filed Apr. 11, 2000 now U.S. Pat. No. 6,228,235 which claims benefit of Ser. No. 60/129,211, filed Apr. 14, 1999.

FIELD OF THE INVENTION

This invention is directed to a method of synthesizing libraries of diverse and complex highly substituted 2,4-dioxopiperidine and novel intermediate compounds. More particularly, the invention relates to a method of solid phase synthesis of (E)-N-substituted-acetyl-N-(2-methoxycarbonyl-3-(Aryl)-prop-2-enyl)amino acids and condensation of the intermediate esters using commercially available Fmoc-protected amino acids on Wang Resins. The invention is further directed to methods for synthesizing the libraries on solid supports. The invention is also directed to methods for identifying and isolating the highly substituted 2,4-dioxopiperidine and novel intermediate compounds with useful and diverse activities from such libraries.

BACKGROUND OF THE INVENTION

Compounds having biological activity can be identified by screening diverse collections of compounds (i.e., libraries of compounds) produced through molecular biology techniques or synthetic chemical techniques.

The generation of chemical libraries on and off solid resins have proven to be a valuable resource for the pharmaceutical industry in their endeavors to discover new drugs using high throughput screening (HTPS) techniques. In creating the libraries, the compounds are ideally synthesized in situ in solution phase or on a solid support. However, relatively simple synthetic methods to produce a diverse collection of such derivatives in situ are often not available.

Such screening methods include methods wherein each member of the library is tagged with a unique identifier tag to facilitate identification of compounds having biological activity or where the library comprises a plurality of compounds synthesized at specific locations on the surface of a solid substrate wherein a receptor is appropriately labeled to identify binding to the compound, e.g., fluorescent or radioactive labels. Correlation of the labeled receptor bound to the substrate with its location on the substrate identifies the binding compound. Using these techniques, the development of efficient high throughput screening has greatly enhanced the pharmaceutical industry's ability to screen large numbers of compounds for biological activity.

Central to these methods is the screening of a multiplicity of compounds in the library and the ability to identify the structures of the compounds that have a requisite biological activity. Preferably, in order to facilitate synthesis and identification, the compounds in the library are typically formed on solid supports wherein the compound is covalently attached to the support via a cleavable or non-cleavable linking arm. In this regard, libraries of diverse compounds are prepared and then screened to identify "lead compounds" having good binding affinity to the receptor.

Pharmaceutical drug discovery relies heavily on studies of structure-activity relationships wherein the structure of "lead compounds" is typically altered to determine the effect of such alteration on activity. Alteration of the structure of the lead compounds permits evaluation of the effect of the structural alteration on activity.

Thus, libraries of compounds derived from a lead compound can be created by including derivatives of the lead compound and repeating the screening procedures. In this manner, compounds with the best biological profile, i.e., those that are most active and which have the most ideal pharmacologic and pharmacokinetic properties, can be identified from the initial lead compound.

Recently various 2,4-Dioxopiperidines were found to be potent as therapeutic or prophylactic agents for hepatic disease, for bacterial and viral infections and for diseases, including AIDS. Eur. Pat. No. 149534; WO 95/14012.

Since 2,4-dioxopiperidines have been shown to possess diverse pharmacological and chemical properties and biological activity in a number of therapeutic areas, the generation of a 2,4-dioxopiperidine compound library would be useful as a screening tool.

Accordingly, in order to develop new pharmaceutical drugs to treat various disease conditions, it would be highly desirable to be able to generate such libraries of substituted 2,4-dioxopiperidine and novel intermediate compounds optionally attached to a solid support. Thus, there is a need for a facile in situ method for the generation of a multiplicity of highly substituted 2,4-dioxopiperidine and novel intermediate compounds.

SUMMARY OF THE INVENTION

The present invention is directed to a process that allows for the assembly of diverse, highly substituted 2,4-dioxopiperidine and novel intermediate compounds using commercially available Fmoc-protected amino acids on solid resins. The rapid synthesis of such highly complex drug like molecules with or without defined stereochemistry is unexpected and surprising.

Accordingly, the invention is directed to a method of synthesizing highly substituted 2,4-dioxopiperidine compounds having the general Formula 1:

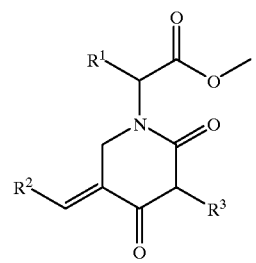

wherein:
$R^1$ is selected from the group consisting of a standard natural amino acid side chain, $CH_3$, $CH(CH_3)CH_2CH_3$ and $CH_2$Phenyl;
$R^2$ is selected from the group consisting of alkyl, substituted alkyl, aralkyl, phenyl and substituted aryl;
$R^3$ is selected from the group consisting of COOalkyl, CN, COloweralkyl, COaralkyl (benzyl and substituted benzyl) and COaryl; where aryl is phenyl, substituted phenyl, thienyl, furyl and napthyl; which method comprises, (a) preparing a compound of the formula:

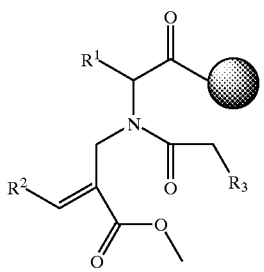

wherein $R^1$ to $R^3$ are as described above, on a solid resin support;

(b) cleaving the compound from the solid resin support and methylating to yield an intermediate methyl ester compound of the formula:

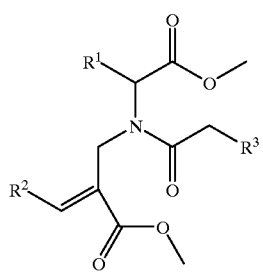

and, (c) condensing the intermediate methyl ester compound to provide the substituted 2,4-dioxopiperidine compounds of Formula 1.

This invention is also directed to highly substituted novel intermediate compounds assembled by the methods of the present invention having the general formula:

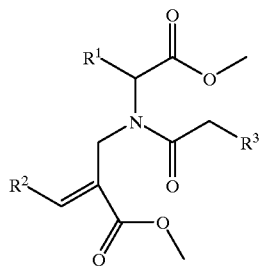

wherein $R^1$ to $R^3$ are as recited above.

In one embodiment of this invention, the amino acid derived novel intermediate precursors are covalently attached to a solid support. Solid supports containing such amino acid derived intermediate precursors may comprise a linking arm which links the solid support to the intermediate precursor. The linking arm can be either cleavable or non-cleavable. The novel intermediate precursors attached to the solid support can be used to prepare a library of solid phase 2,4-dioxopiperidine derivatives.

The methods described above can be used to create a library of diverse dioxopiperidine derivatives. Accordingly, in one of its composition aspects, this invention is directed to a library of diverse (E)-N-substituted-acetyl-N-(2-methoxycarbonyl-3-(Aryl)-prop-2-enyl)amino acid derivatives comprising a plurality of solid supports having a plurality of covalently bound (E)-N-substituted-acetyl-N-(2-methoxycarbonyl-3-(Aryl)-prop-2-enyl)amino acid derivatives, wherein the derivatives bound to each of said supports is substantially homogeneous and further wherein the derivatives bound on one support is different from the derivatives bound on the other supports. The library is screened to isolate individual compounds that bind to a receptor or possess some desired property.

DETAILED DESCRIPTION OF THE INVENTION

Relative to the above generic description, certain compounds of the general formulae are preferred.

Particularly preferred embodiments are those compounds in which:

$R^1$ is selected from the group consisting of a standard natural amino acid side chain, $CH_3$, $CH(CH_3)CH_2CH_3$ and $CH_2$ Phenyl;

$R^2$ is selected from the group consisting of alkyl, aralkyl, phenyl and substituted phenyl; where the substituents on the substituted phenyl group are selected from lower alkyl, halo, alkoxy, nitrile, cyano, alkoxycarbonyl, aryloxycarbonyl, nitro, furyl and substituted furyl; where the substituents on the substituted furyl group are selected from alkyl, halo, alkoxy, alkoxycarbonyl, nitrile, aryloxycarbonyl, nitro, thienyl and substituted thienyl; where the substituents on the substituted thienyl group are selected from lower alkyl, halo, alkoxy, nitrile, alkoxycarbonyl, aryloxycarbonyl, naphthyl and substituted naphthyl; where the substituents on the substituted naphthyl group are selected from lower alkyl, halo, alkoxy, nitrile, alkoxycarbonyl and aryloxycarbonyl; and, $R^3$ is selected from the group consisting of COOalkyl, CN, COloweralkyl, COaralkyl (benzyl and substituted benzyl) and COaryl; where aryl is phenyl, substituted phenyl, thienyl, furyl and napthyl.

Preferred embodiments are those compounds wherein:

$R^1$ is selected from the group consisting of $CH_3$, $CH(CH_3)CH_2CH_3$ and $CH_2$ Ph;

$R^2$ is selected from the group consisting of phenyl, halophenyl, cyanophenyl and carboxyphenyl; and, $R^3$ is selected from the group consisting of $COOC_2H_5$, CN and $COCH_3$.

DEFINITIONS

Listed below are definitions of various terms used to describe this invention. These definitions apply to the terms as they are used throughout this specification, unless otherwise limited in specific instances, either individually or as part of a larger group.

The standard amino acid side chain for $R^1$ may be selected from any of the known natural amino acid groups such as alanine, arginine, asparagine, aspartic acid, cysteine, glutamine, isoleucine, glycine, leucine, histidine, methionine, lysine, phenylalanine, proline, serine, valine, threonine, tryptophane, tyrosine, and the like.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyl, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamine, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g.CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidyl, pyridyl, pyrimidyl and the like. Where noted above that the substituent is further substituted, such substitutions will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, cycloalkyl, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, nitrile, cyano, carboxy, carboxyalkyl, carbamyl, alkoxycarbonyl, alkylthiono, arylthiono, alkysulfonyl, sulfonamido, aryloxy, alkoxycarbonyl, nitrile, furyl and the like. The substituent may be further substituted by halo, hydroxy, alkyl, alkoxy, alkoxycarbonyl, nitrile, aryl, aryloxycarbonyl, substituted aryl, substituted alkyl, aralkyl, heterocyclyl and substituted heterocyclyl. "Substituted benzyl" refers to a benzyl group substituted by, for example, any of the groups listed above for substituted aryl.

The term "cycloalkyl" refers to optionally substituted, saturated cyclic hydrocarbon ring systems, preferably containing 1 to 3 rings and 3 to 7 carbons per ring which may be further fused with an unsaturated $C_3$ to $C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above or one or more groups described above as alkyl substituents.

The terms "heterocycle", "heterocyclic" and "heterocyclo" refer to an optionally substituted, fully saturated or unsaturated, aromatic or nonaromatic cyclic group. Such group, for example, can be a 4 to 7 membered monocyclic, a 7 to 11 membered bicyclic or a 10 to 15 membered tricyclic ring system which has at least one heteroatom in at least one carbon atom containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and where the nitrogen heteroatoms may also optionally be quaternized. The heterocyclic group may be attached at any heteroatom or carbon atom.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thizaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropryanyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, triazolyl and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl), or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl and the like.

Exemplary substituents include one or more alkyl groups as described above or one or more groups described above as alkyl substituents.

The term "heteroatoms" shall include oxygen, sulfur and nitrogen.

Throughout this specification, certain abbreviations are employed which have the following meanings, unless specifically indicated otherwise: DMF is N,N-dimethyl formamide, MeOH is methanol, THF is tetrahydrofuran, DME is ethylene glycol dimethyl ether, NBS is N-bromosuccinimide, Fmoc is N-(9-fluorenylmethoxycarbonyl), NOE is Nuclear Overhauser Enhancement, DMS is dimethyl sulfide, DMAP is dimethylaminopyridine, DABCO is 1,4-diazabicyclo[2.2.2] octane, DIC is diisopropylcarbodimide, TFA is trifluoroacetic acid and $TMSCHN_2$ is trimethylsilyldiazomethane.

General Synthetic Method

Representative compounds of the present invention are synthesized in accordance with the general method described below and illustrated in Scheme 1. Since Scheme 1 is an illustration, the invention should not be construed as being limited by the chemical reactions and conditions expressed.

Various publications are cited throughout the description for this general scheme. The disclosure of these publications is hereby incorporated by reference into this application to describe more fully the state of the art to which this invention pertains.

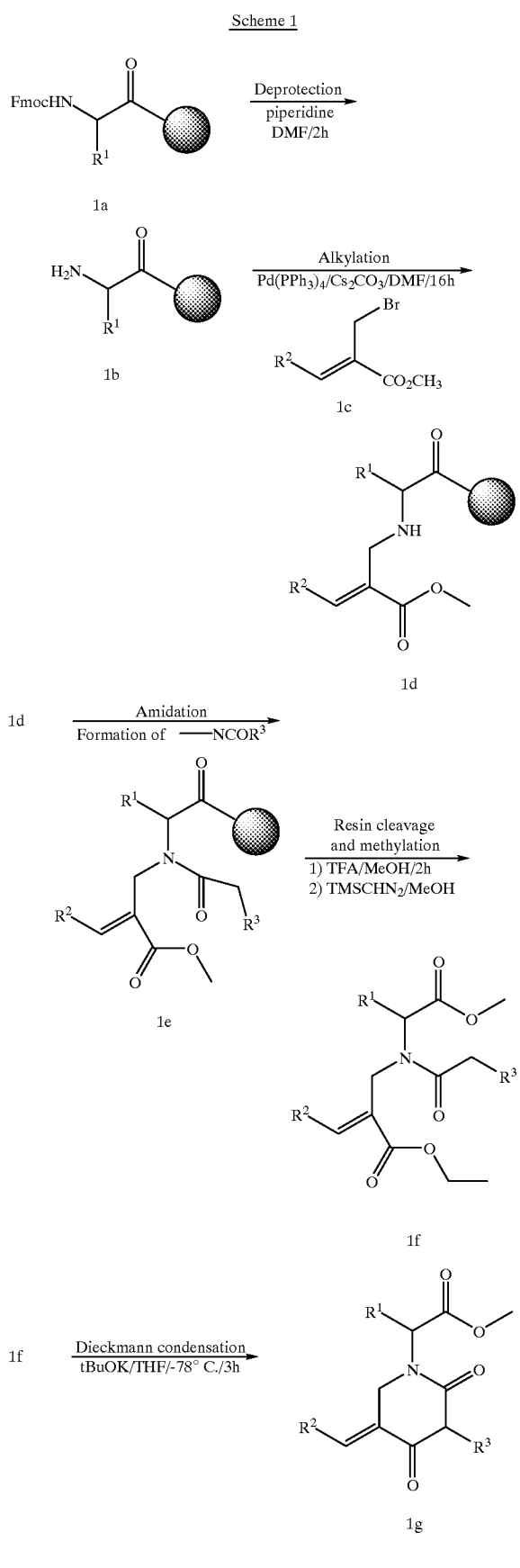

Scheme 1

This invention is directed to the solid phase synthesis of diverse, highly substituted 2,4-dioxopiperidine Compounds 1 g from intermediate (E)-N-substituted-acetyl-N-(2-methoxycarbonyl-3-(Aryl)-pro p-2-enyl)amino acid Compounds 1f using commercially available Fmoc-protected amino acid Compounds 1a on Wang Resins. The synthesis requires an alkylation and subsequent amidation step The use of the Fmoc-protected amino acids on Wang Resins and the alkylation and amidation steps provides unique and novel diversity to the highly substituted 2,4-dioxopiperidine Compounds 1g and intermediate Compounds 1f.

This approach can be used to generate a number of compound libraries of both the highly substituted 2,4-dioxopiperidine Compounds 1g and the highly substituted intermediate Compounds 1f with the three diversity elements $R^1$, $R^2$ and $R^3$. By condensing the highly substituted intermediate Compounds If, the intermediate esters can be further elaborated to the various highly substituted 2,4-dioxopiperidine Compounds 1g.

The solid phase synthesis was initiated with the deprotection of the Fmoc-protected amino acid Compound 1a on Wang Resins (1, 2). Piperidine in DMF was added and the reaction was run for about 2 h at about room temperature. Various commercially available Fmoc-amino acid-Wang Resin units provide the subsequent diversity element in $R^1$ of the intermediate Compounds 1f and 2,4-dioxopiperidine Compounds 1g.

After removal of the Fmoc group from Compound 1a, alkylation of the free amine Compounds 1b was accomplished by a palladium (0) catalyzed reaction with methyl 2-(Z)-(bromomethyl)-3-aryl-prop-2-enoate Compounds 1c in DMF run for about 16 h at about room temperature.

The bromide Compounds 1c were synthesized in two steps. The first step is a DABCO catalyzed Baylis-Hillman's reaction of methyl acrylate with the appropriate aldehyde (3, 4), run for about 6 h at about 0° C. and then stirred at about room temperature for about 16 h. The second step involves a Corey-Kim bromination using NBS-DMS (5, 6) in $CH_2Cl_2$ cooled to about 0° C. and stirred for about 1 h. The solution of Compound 1b was added and stirred for diversity element in $R^2$ of the intermediate Compounds 1f and 2,4-dioxopiperidine Compounds 1g.

The subsequent amidation step generates the third diversity element in $R^3$ of the intermediate Compounds if and 2,4-dioxopiperidine Compounds 1g. By using different amidating reagents and conditions, such as stirring with ethylmalonyl chloride in DMAP and $CH_2Cl_2$ for about 16 h at about 25° C. or stirring with cyanoacetic acid and DIC in DMF for about 50 h at about 25° C. or stirring with diketene for about 50 h at about 25° C., the compounds, respectively, α-carboethoxyamide (7), α-cyanoamide (8) and α-ketoamide (9) can be produced.

After resin cleavage with $CF_3COOH/MeOH$ by stirring for about 2 h at about 25° C. and methylation with $TMSCHN_2$ in MeOH, the intermediate methyl ester Compounds 1f were obtained. The total yield for the reaction sequence from Compounds 1a to Compounds 1f is from about 28% to about 31%.

Dieckmann condensation of intermediate Compounds 1f with t-BuOK in THF stirred for about 3 h at about −78° C. provided 2,4-dioxopiperidine Compounds 1 g in yields from about 60% to about 72% (10, 11).

Compounds 1f and Compounds 1g were characterized by $^1$HNMR, $^{13}$C NMR and ESMS. The (E)/(Z) configurations were determined by NOE experiments.

The synthesis of specific, representative compounds of the present invention is presented in detail in the following examples. These examples are intended to illustrate the methods of synthesis and are not intended to limit the scope of the claims in any way. Moreover, no attempt has been made to optimize the yields obtained in these reactions. It would be obvious to one skilled in the art that variations in reaction times, temperatures, solvents, and/or reagents could increase the yields.

EXAMPLE 1

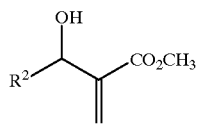

General Procedure for Preparing Methyl 2-(Hydroxy(aryl)methyl)prop-2-enoate

A solution of aryl aldehyde (10 mmol) and methyl acrylate (10 mmol) in dioxane (1 mL) was cooled to about 0° C. in an ice bath, and DABCO (100 mg, 0.9 mmol) was added. The reaction was kept cold for about 6 h. Then the reaction mixture was stirred at about room temperature for about 16 h. After concentration, chromatography of the residue afforded the title compound in yields from about 64% to about 68%.

EXAMPLE 1a

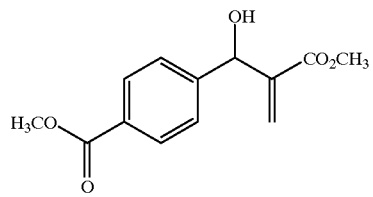

Data for Methyl 2-(Hydroxy-(4-methoxycarbonylphenyl)methyl)prop-2-enoate $^1$H NMR (CDCl$_3$, 500 MHz) δ 8.02–8.00 (d, 2H, J=8.2 Hz), 7.46–7.45 (d, 2H, J=82 Hz), 6.36 (s, 1H), 5.82 (s, 1H) 5.60 (s, 1H), 3.91 (s, 3H) 3.73 (s, 3H) $^{13}$C NMR (CDCl$_3$, 500 MHz) δ 167.1, 166.8, 146.5, 141.6, 130.0, 129.8, 127.0, 126.7, 73.3, 52.33, 52.29. EIMS m/z 273 (M+Na$^+$).

EXAMPLE 1b

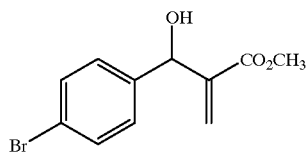

Data for Methyl 2-((4-Bromocarbonylphenyl)hydroxymethyl)prop-2-enoate $^1$H NMR (CDCl$_3$, 500 MHz) δ 7.48–7.46 (d, 2H, J=8.3 Hz), 7.27–7.25 (d, 2H, J=8.3 Hz), 6.34 (s, 1H), 5.82 (s, 1H), 5.51 (s, 1H), 3.73 (s, 3H). $^{13}$C NMR (CDCl$_3$, 500 MHz) δ 166.8, 141.7, 140.5, 131.7, 128.5, 126.6, 121.9, 72.9, 52.2. EIMS m/z 295 (M+Na$^+$).

EXAMPLE 2

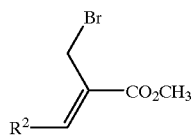

General Procedure for Preparing Methyl 2-(Z)-(Bromomethyl)-3-Aryl-prop-2-enoate

N-bromosuccinimide (4.4 mmol) in dry CH$_2$Cl$_2$ (8 mL) was cooled to about 0° C. and DMS (5 mmol) was added. The yellow slurry was stirred for about 1 h. The solution of methyl 2-(hydroxy(aryl)methyl)prop-2-enoate (4 mmol) prepared in Example 1 was combined with CH$_2$Cl$_2$ (5 mL) and the resulting suspension was stirred for about 20 h at about room temperature. After concentration, chromatography of the residue afforded the title compound in yields from about 86% to about 99%.

EXAMPLE 2a

General Procedure for Preparing Methyl 2-(Z)-(Bromomethyl)-3-(4-bromophenyl)prop-2enoate Using the procedure of Example 2, and the solution of methyl 2-(hydroxy(aryl)methyl)prop-2-enoate (4 mmol) prepared in Example 1, where R$^2$ is bromine, the reaction affords the title compound.

EXAMPLE 2b

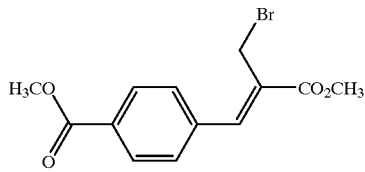

Data for Methyl 2-(Z)-(Bromomethyl)-3-(4-methoxycarbonylphenyl)prop-2-enoate $^1$H NMR (CDCl$_3$, 500 MHz) δ 8.13–8.11 (d, 2H, J=8.2 Hz), 7.83(s, 1H), 7.63–7.42 (d, 2H, J=8.2 Hz), 4.35 (s, 2H), 3.94 (s, 3H), 3.90 (s, 3H). $^{13}$C NMR (CDCl$_3$, 500 MHz) δ 166.6, 166.5, 141.7, 138.8, 131.0, 130.7, 130.2, 129.6, 52.9, 52.6, 26.2. EIMS m/z 335 (M+Na$^+$) (the (Z) configuration is supported by NOE experiment results).

EXAMPLE 2c

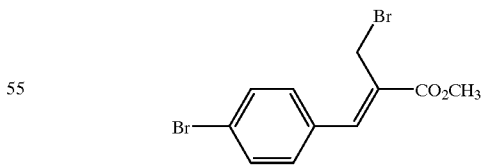

Data for Methyl (Z)-3-(4-Bromocarbonylphenyl)-2-(Bromomethyl)prop-2enoate $^1$H NMR (CDCl$_3$, 500 MHz) δ 7.74 (s, 1H), 7.61–7.59 (d, 2H, J=8.3 Hz), 7.45–7.43 (d, 2H, J=8.3 Hz), 4.35 (s, 2H), 3.88 (s, 3H). $^{13}$C NMR (CDCl$_3$, 500 MHz) δ 166.6, 141.8, 133.2, 132.4, 131.3, 129.5, 124.3, 52.8, 26.5. EIMS m/z 357 (M+Na$^+$).

EXAMPLE 3

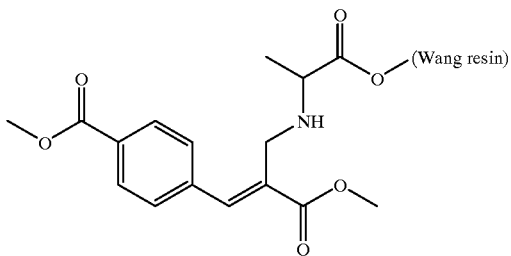

Attachment of Methyl 2-(Z)-(Bromomethyl)-3-(4-methoxycarbonylphenyl)prop-2enoate to Fmoc-Ala-Wang Resin To Fmoc-Ala-Wang Resin (Novabiochem, 0.74 mmol/g) (1 g, 0.74 mmol) was added a solution containing 5 mL each of DMF and piperidine at about room temperature. The suspension was allowed to mix at about room temperature for about 2 h. The supernatant was then removed. The resin was washed with DMF, MeOH, $CH_2Cl_2$, and dried in vacuo. To the dried resin were added the methyl 2-(Z)-(Bromomethyl)-3-(4-methoxycarbonylphenyl)prop-2-enoate (231 g, 0.74 mmol) prepared in Example 2a, $Pd(PPh_3)_4$ (8.6 mg, 0.0074 mmol), $Cs_2CO_3$ (241 mg, 0.74 mmol) and DMF (10 mL) at about room temperature. The suspension was allowed to mix at about room temperature for about 16 h. After about 16 h, the supernatant was removed. The resin was washed with DMF, MeOH and $CH_2Cl_2$ and then dried in vacuo.

EXAMPLE 3a

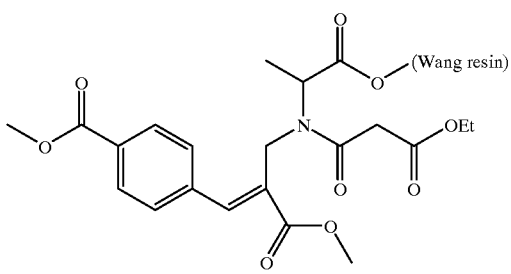

Attachment of Ethyl 3-Chloro-3-oxopropionate to the Alkylated Fmoc-Ala-Wang Resin A mixture of the resin prepared in Example 3, pyridine (120 µL, 1.48 mmol) and DMAP (0.9 mg, 0.0074 mmol) in $CH_2Cl_2$ (10 mL) was stirred at about 0° C. for about 20 min. Ethyl 3-chloro-3-oxopropionate (188 µL, 1.48 mmol) was added. The suspension was stirred for about 16 h at about 25° C. before the supernatant was removed. The resin was washed with MeOH and $CH_2Cl_2$ and dried in vacuo.

EXAMPLE 3b

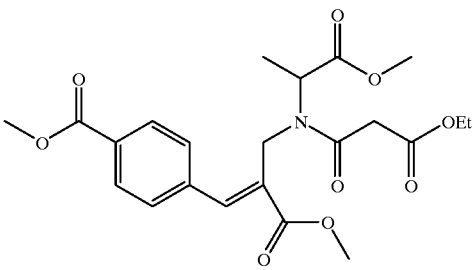

Preparation of and Data for Methyl (E)-N-Ethoxycarbonylacetyl-N-(2-methoxycarbonyl-3-(4-methoxycarbonylphenyl)prop-2-enyl)-2-aminopropionate To the resin prepared in Example 3a, TFA (10 mL) was added. The suspension was stirred for about 2 h at about 25° C. Then the supernatant was removed and the resin was washed with MeOH (3×8 mL). The combined supernatants were concentrated and dried in vacuo. The residue was dissolved again in MeOH (10 mL) and (trimethylsilyl)diazomethane (2.0 M solution in hexanes) was added dropwise until the yellow color stayed. After concentration, chromatography (EtOAc/hexane) of the crude yellow oil afforded 100 mg of the title compound (total yield of about 30% from Example 3 to Example 3b). $^1H$ NMR ($CD_3OD$, 500 MHz) δ 8.10–8.08 (d, 2H, J=8.2 Hz), 7.96 (d, 1 H,), 7.50–7.48 (d, 2H, J=8.2 Hz), 4.60–4.56 (d, 1 H, J=15.5 Hz), 4.48–4.45 (d, 1H, J=15.5 Hz), 4.17–4.12 (m, 2H), 3.93 (s, 3H), 3.87 (s, 3H), 3.80–3.60 (m, 3H), 3.57 (s, 3H), 1.26–1.23 (t, 3H, J=6.9 Hz), 1.18–1.16 (d, 3H, J 6.9 Hz). $^{13}C$ NMR ($CD_3OD$, 500 MHz) δ 172.8, 169.3, 169.1, 168.4, 167.9, 143.6, 140.2, 132.0, 131.5, 131.0, 130.6, 62.6, 56.2, 53.0, 52.9, 52.7, 46.0, 42.1, 14.5, 13.9. EIMS m/z 472 ($M+Na^+$).

EXAMPLE 3c

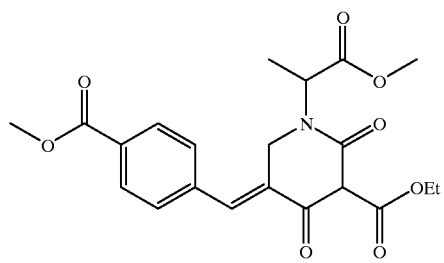

Preparation of and Data for 2,4-(E)-Dioxo-3-(ethoxycarbonyl)-N-(methoxycarbonyl(methyl)methyl)-5-(2-(4-methoxycarbonylphenyl)ethylene)piperidine The compound prepared in Example 3b (83 mg, 0.185 mmol) was placed in THF (10 mL) and cooled to about −78° C. Potassium tert-butoxide (1.0 M solution in 2-methyl-2-propanol) (0.5 mL, 0.5 mmol) was added. The mixture was stirred for about 3 h at about −78° C. The reaction mixture was quenched by saturated $NH_4Cl$ solution (10 mL). The organic layer was removed. The aqueous layer was extracted by EtOAc (2×10 mL). The combined organic layers were washed by saturated NaCl solution (20 mL), dried over Na$_2$SO$_4$ and concentrated. Chromatography (CH$_2$Cl$_2$/MeOH) of the crude yellow oil afforded 50 mg (64% yield) of the title compound. $^1$H NMR (Pyridine-d$_5$ 500 MHz) δ 8.10–8.09 (d, 2H, J=8.0 Hz), 7.90 (s, 1 H), 7.82–7.81 (d, 2H, J=8.0 Hz), 5.10–5.07 (d, 1H, J=14.6 Hz), 4.55–4.53 (d, 1H, J=14.6 Hz), 4.33–4.29 (dd, 2H, J=6.8 Hz), 3.87 (broad, 1 H), 3.81 (s, 3H), 3.71 (s, 3H), 1.38–1.37 (d, 3H, J=6.4 Hz), 1.24–1.23 (t, 3H, J=6.8 Hz). $^{13}$C NMR (CD$_3$OD, 500 MHz) δ 196.5, 175.4, 169.5, 168.2, 167.7, 141.6, 140.9, 132.4, 131.4, 130.9, 130.7, 90.7, 59.4, 53.0 (2C), 52.9, 37.3, 16.8, 15.2. EIMS m/z 418 (M+H$^+$), 440 (M+Na$^+$).

EXAMPLE 4

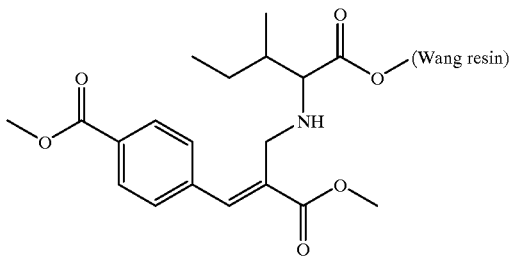

Attachment of Methyl 2-(Z)-(Bromomethyl)-3-(4-metheoxycarbonylphenyl)prop-2-enoate to Fmoc-Ile-Wang Resin To Fmoc-Ile-Wang Resin (Novabiochem, 0.62 mmol/g) (1 g, 0.62 mmol) was added a solution containing 5 mL each of DMF and piperidine at about room temperature. The suspension was allowed to mix at about room temperature for about 2 h. The supernatant was then removed. The resin was washed with DMF, MeOH, CH$_2$Cl$_2$, and dried in vacuo. To the dried resin were added methyl 2-(Z)-(Bromomethyl)-3-(4-methoxycarbonylphenyl)prop-2-enoate (193 g, 0.62 mmol) prepared in Example 2a, Pd(PPh$_3$)$_4$ (7.2 mg, 0.0062 mmol), Cs$_2$CO$_3$ (202 mg, 0.62 mmol) and DMF (10 mL) at about room temperature.

The suspension was allowed to mix for about 16 h at about 25° C. before supernatant was removed. The resin was washed with DMF, MeOH, and CH$_2$Cl$_2$ and then dried in vacuo.

EXAMPLE 4a

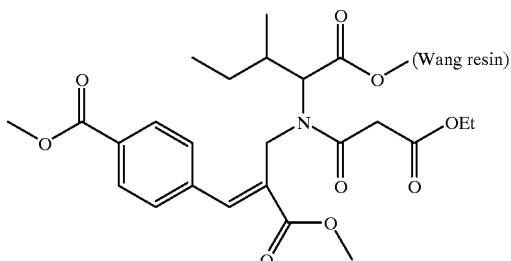

Attachment of Ethyl 3-Chloro-3-oxopropionate to the Alkylated Fmoc-Ile-Wang Resin A mixture of the resin prepared in Example 4, pyridine (100 μL, 1.24 mmol) and DMAP (0.8 mg, 0.0062 mmol) in CH$_2$Cl$_2$ (10 mL) was stirred at about 0° C. Ethyl 3-chloro-3-oxopropionate (158 μL, 1.24 mmol) was added. The suspension was stirred for about 16 h at about 25° C. before the supernatant was removed. The resin was washed with MeOH and CH$_2$Cl$_2$ and dried in vacuo.

EXAMPLE 4b

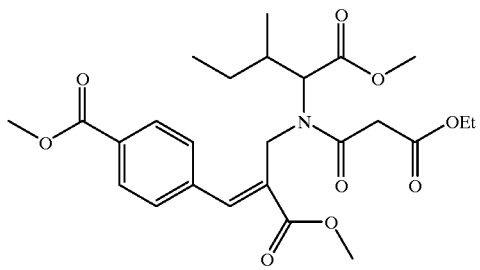

Preparation of and Data for Methyl (E)-N-Ethoxycarbonylacetyl-N-(2-methoxycarbonyl-3-(4-methoxycarbonylphenyl)prop-2-enyl)-2-amino(3-methyl)pentanate To the resin prepared in Example 4a, TFA (10 mL) was added. The suspension was stirred for about 2 h at about 25° C. The supernatant was then removed and the resin was washed with MeOH (3×8 mL). The combined supernatants were concentrated and dried in vacuo. The residue was dissolved again in MeOH (10 mL) and (trimethylsilyl)diazomethane (2.0 M solution in hexanes) was added dropwise until the yellow color stayed. After concentration, chromatography (EtOAc/hexane) of the crude yellow oil afforded 93 mg of the title compound (total yield of about 31% from Example 4 to Example 4b). $^1$H NMR (CD$_3$OD, 500 MHz) δ 8.12–8.10 (d, 2H, J=8.2 Hz), 8.03 (d, 1H), 7.50–7.48 (d, 2H, J=8.2 Hz), 4.65–4.62 (d, 1 H, J=15.5 Hz), 4.43–4.40 (d, 1H, J=15.5 Hz), 4.19–4.15 (dd, 2H, J=7.2 Hz), 3.94 (s, 3H), 3.87 (s, 3H), 3.54 (s, 3H), 3.35 (s, 2H), 3.20–3.18 (d, 1H, J=9.4 Hz) 2.05–1.95 (m, 1H), 1.40–1.20 (m, 1H), 1.28–1.25 (t, 3H, J=7.2 Hz), 0.71–0.69 (d, 3H, J=6.3 Hz), 0.66–0.63 (t, 3H, J=7.4 Hz), 0.60–0.50 (m, 1H). $^{13}$C NMR (CD$_3$OD, 500 MHz) δ 171.7, 169.6, 169.4, 168.3, 167.9, 144.3, 140.6, 131.9, 131.2, 131.0, 130.6, 64.5, 62.6, 53.0 (3C based on HMQC experiment result), 52.4, 46.6, 35.1, 25.8, 17.9, 14.6, 11.8. EIMS m/z492 (M+H$^+$), 514 (M+Na$^+$).

EXAMPLE 4c

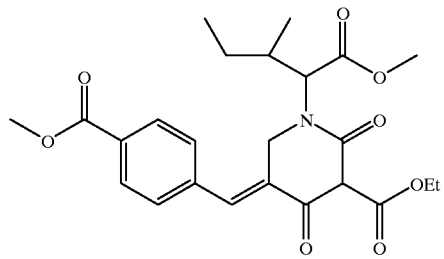

Preparation of and Data for 3-(E)-(Ethoxycarbonyl)-2,4-dioxo-N-(methoxycarbonyl(2-(methyl)propyl)methyl)-5-(2-(4-methoxycarbonylphenyl)ethylene)piperidine The compound prepared in Example 4b (45 mg, 0.092 mmol) in THF (5 mL) was cooled down to about –78° C.

Potassium tert-butoxide (1.0 M solution in 2-methyl-2-propanol) (0.3 mL, 0.3 mmol) was added. The mixture was stirred for about 3 h at about −78° C. The reaction mixture was quenched by saturated NH₄Cl solution (5 mL). The organic layer was removed. The aqueous layer was extracted by EtOAc (2×10 mL). The combined organic layers were washed by saturated NaCl solution (20 mL), dried over Na₂SO₄ and concentrated. Chromatography (CH₂Cl₂/MeOH) of the crude yellow oil afforded 25 mg (60% yield) of the title compound. ¹H NMR (Pyridine-d₅, 500 MHz) δ 8.10–8.08 (d, 2H, J=7.9 Hz), 7.91 (s, 1H,), 7.83–7.82 (d, 2H, J=7.9 Hz), 5.28–5.25 (d, 1H, J=14.8 Hz), 4.50–4.47 (d, 1H, J=14.8 Hz), 4.30–4.28 (m, 2H), 3.87 (d, 1 H, J=2.5 Hz), 3.80 (s, 3H), 3.72 (s, 3H), 2.05–1.90 (m, 2H), 1.80 (m, 1H), 1.23–1.20 (t, 3H, J=7.0 Hz), 0.94–0.91 (t, 3H, J=7.3 Hz), 0.90–0.89 (d, 3H, J=6.7 Hz). ¹³C NMR (CD₃OD, 500 MHz) 6195.4, 175.6, 169.3, 168.1, 167.7, 142.2, 135.0, 132.9, 132.5, 130.5, 124.4, 74.3, 67.2, 53.0 (3C), 37.0, 36.6, 26.3, 13.4, 12.8. EIMS m/z460 (M+H⁺), 482 (M+Na⁺).

EXAMPLE 5

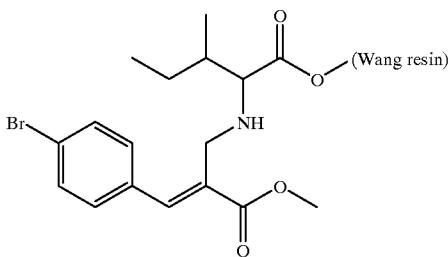

Attachment of Methyl 2-(Z)-(Bromomethyl)-3-(4-bromophenyl)prop-2-enoate to Fmoc-Ile-Wang Resin To Fmoc-Ile-Wang Resin (Novabiochem, 0.38 mmol/g) (2 g, 0.76 mmol) was added a solution containing 10 mL-each of DMF and piperidine at about room temperature. The suspension was allowed to mix at about room temperature for about 2 h. The supernatant was then removed. The resin was washed with DMF, MeOH, CH₂Cl₂ and dried in vacuo. To the dried resin were added the methyl 2-(Z)-(Bromomethyl)-3-(4-bromolphenyl)prop-2-enoate (279 g, 0.836 mmol) prepared in Example 2a, Pd(PPh₃)₄ (8.8 mg, 0.0076 mmol), Cs₂CO₃ (272 mg, 0.836 mmol) and DMF (10 mL) at about room temperature. The suspension was allowed to mix for about 16 h at about 25° C. before supernatant was removed. The resin was washed with DMF, MeOH and CH₂Cl₂ and then dried in vacuo.

EXAMPLE 5a

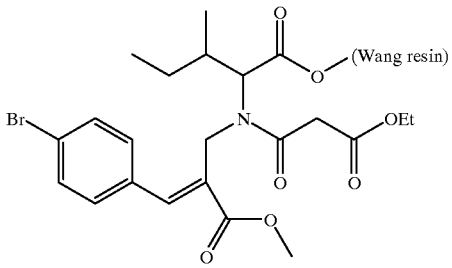

Attachment of Ethyl 3-Chloro-3-oxopropionate to the Alkylated Fmoc-Ile-Wang Resin A mixture of the resin prepared in Example 5, pyridine (123 μL, 1.52 mmol) and DMAP (0.9 mg, 0.0076 mmol) in CH₂Cl₂ (20 mL) was stirred at about 0° C. Ethyl 3-chloro-3-oxopropionate (194 μL, 1.52 mmol) was added. The suspension was stirred for about 16 h at about 25° C. before the supernatant was removed. The resin was washed with MeOH and CH₂Cl₂ and dried in vacuo.

EXAMPLE 5b

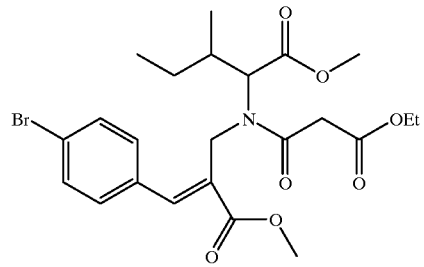

Preparation of and Data for Methyl(E)-N-ethoxycarbonylacetyl-N-(2-methoxycarbonyl-3-(4-bromophenyl)prop-2-enyl)-2-amino(3-methyl) pentanate To the resin prepared in Example 5a, TFA (10 mL) was added. The suspension was stirred for about 2 h at about 250C. The supernatant was then removed and the resin was washed with MeOH (3×8 mL). The combined supernatants were concentrated and dried in vacuo. The residue was dissolved again in MeOH (10 mL) and (trimethylsilyl)diazomethane (2.0 M solution in hexanes) was added dropwise until the yellow color stayed. After concentration, chromatography (EtOAc/hexane) of the crude yellow oil afforded 110 mg of the title compound (total yield of about 28% from Example 5 to Example 5b). ¹H NMR (CD₃OD, 500 MHz) δ 7.94 (s, 1 H), 7.65–7.63 (d, 2H, J=8.3 Hz), 7.30–7.29 (d, 2H, J=8.3 Hz), 4.624.59 (d, 1 H, J=15.5 Hz), 4.42–4.39 (d, 1H, J=15.5 Hz), 4.19–4.15 (dd, 2H, J=7.2 Hz), 3.85 (s, 3H), 3.54 (s, 3H), 3.35 (s, 2H), 3.90–3.60 (m, 2H), 3.21–3.19 (d, 1H, J=9.4 Hz), 2.05–1.95 (m, 1 H), 1.40–1.20 (m, 1 H), 1.29–1.25 (t, 3H, J=7.2 Hz), 0.73–0.72 (d, 3H, J=6.5 Hz), 0.66–0.63 (t, 3H, J=7.3 Hz), 0.60–0.50 (m, 1H). ¹³C NMR (CD₃OD, 500 MHz) δ 171.8, 169.5, 169.4, 168.5, 144.3, 134.8, 133.3, 132.3, 130.3, 124.6, 64.5, 62.6, 52.9 (2C), 52.4, 46.5, 35.1, 25.9, 17.9, 14.6, 11.8. EIMS m/z 534 (M+Na⁺).

EXAMPLE 5c

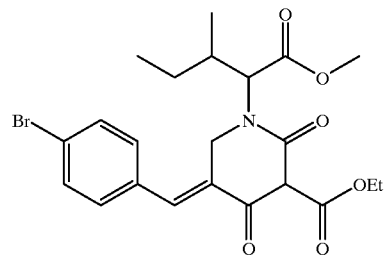

Preparation of and Data for 5-(E)-(2-(4-Bromophenyl)ethylene)-3-(ethoxycarbonyl)-2,4-dioxo-N-(methoxycarbonyl(2-(methyl)propyl) methyl)piperidine The compound prepared in Example 5b (90 mg, 0.176 mmol) in THF (10 mL) was cooled down to about −78° C.

Potassium tert-butoxide (1.0 M solution in 2-methyl-2-propanol) (0.5 mL, (0.5 mmol) was added. The mixture was stirred for about 3 h at about −78° C. The reaction mixture was quenched by saturated NH$_4$Cl solution (10 mL) The organic layer was removed. The aqueous layer was extracted by EtOAc (2×10 mL). The combined organic layers were washed by saturated NaCl solution (20 mL), dried over Na$_2$SO$_4$ and concentrated. Chromatography (CH$_2$Cl$_2$/MeOH) of the crude yellow oil afforded 61 mg (72% yield) of the title compound. $^1$H NMR (Pyridine-d$_5$, 500 MHz) δ 7.83 (s, 1H), 7.66–7.65 (d, 2H, J=8.1 Hz), 7.50–7.49 (d, 2H, J=8.1 Hz), 5.21–5.18 (d, 1H, J=14.8 Hz), 4.50–4.48 (d, 1H, J=14.8 Hz), 4.32–4.30 (m, 2H), 3.84 (d, 1H, J=2.5 Hz), 3.71 (s, 3H), 2.05–1.90 (m, 2H), 1.80 (m, 1H), 1.24–1.21 (t, 3H, J=Hz), 0.94–0.91 (t, 3H, J=7.3 Hz), 0.90–0.89 (d, 3H, J=6.7 Hz). $^{13}$C NMR (CD$_3$OD, 500 MHz) δ 195.4, 175.6, 169.3, 167.6, 142.2, 135.0, 132.9, 1321, 130.5, 124.4, 74.3, 67.2, 59.3, 53.0 (2C), 37.0, 36.6, 26.3, 13.4, 12.8. EIMS m/z 433 (M+H$^+$), 455 (M+Na$^+$).

EXAMPLE 6

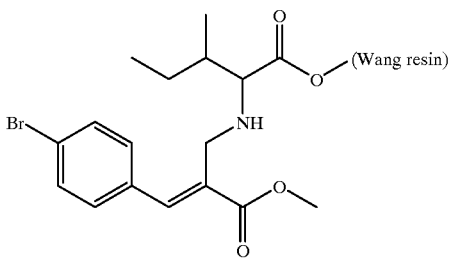

Attachment of Methyl 2-(Z)-(Bromomethyl)-3-(4-bromophenyl)prop-2-enoate to Fmoc-lle-Wang Resin To Fmoc-lle-Wang Resin (Novabiochem, 0.38 mmol/g) (1 g, 0.38 mmol) was added a solution containing 5 mL each of DMF and piperidine at about room temperature. The suspension was allowed to mix at about room temperature for about 2 h before the supernatant was removed. The resin was washed with DMF, MeOH, CH$_2$CH$_2$Cl$_2$ and dried in vacuo. To the dried resin were added the methyl 2-(Z)-(Bromomethyl)-3-(4-bromolphenyl)prop-2-enoate (139 g, 0.418 mmol) prepared in Example 2a, Pd(PPh$_3$)$_4$ (4.4 mg, 0.0038 mmol), Cs$_2$CO$_3$ (138 mg, 0.418 mmol) and DMF (10 mL) at about room temperature. The suspension was allowed to mix for about 16 h at about 25° C. before the supernatant was removed. The resin was washed with DMF, MeOH and CH$_2$Cl$_2$ and then dried in vacuo.

EXAMPLE 6a

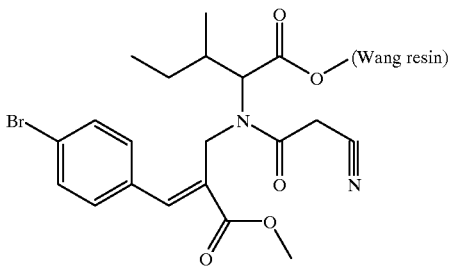

Attachment of Cyanoacetic Acid to the Alkylated Fmoc-lle-Wang Resin

A mixture of the resin prepared in Example 6 and DIC (119 μl, 0.76 mmol) in CH$_2$Cl$_2$ (5 mL) was stirred about 0° C. Cyanoacetic acid (64 mg, 0.76 mmol) was added. The suspension was stirred for about 50 h at about 25° C. before the supernatant was removed. The resin was washed with MeOH and CH$_2$Cl$_2$ and dried in vacuo.

EXAMPLE 6b

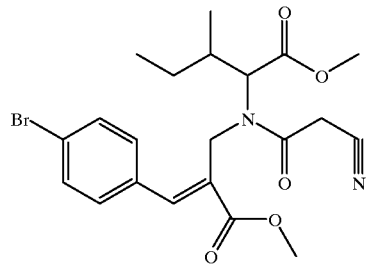

Preparation of and Data for Methyl(E)-N-cyanoacetyl-N-(2-methoxycarbonyl)-3-(4-bromophenyl)-prop-2-enyl)-2-amino(3-methyl) pentanate To the resin prepared in Example 6a, TFA (5 mL) was added. The suspension was stirred for about 2 h at about 25° C. The supernatant was then removed and the resin was washed with MeOH (3×8 mL). The combined supernatants were concentrated and dried in vacuo. The residue was dissolved again in MeOH (10 mL) and (trimethylsilyl) diazomethane (2.0 M solution in hexanes) was added dropwise until the yellow color stayed. After concentration, chromatography (EtOAc/hexane) of the crude yellow oil afforded 50 mg of the title compound (total yield of about 28% from Example 6 to Example 6b). $^1$H NMR (CD$_3$OD, 500 MHz) δ 7.96 (s, 1H), 7.65–7.64 (d, 2H, J=8.3 Hz), 7.30–7.28 (d, 2H, J=8.3 Hz), 4.49–4.46 (d, 1H, J=15.5 Hz), 4.38–4.35 (d, 1H, J=15.5 Hz), 3.87 (s, 3H), 3.55 (s, 3H), 3.80–3.60 (m, 2H), 3.22–3.21 (d, 1H, J=9.4 Hz), 2.00–1.85 (m, 1H), 1.30–1.15 (m, 1H), 0.72–0.71 (d, 3H, J=6.4 Hz), 0.70–0.67 (t, 3H, J=7.3 Hz), 0.60–0.50 (m, 1H). $^{13}$C NMR (CD$_3$OD, 500 MHz) δ 171.4, 168.5, 165.9 144.6, 134.7, 133.3, 132.2 129.7, 124.7, 116.1, 64.7, 53.1 (2C), 52.5, 46.1, 34.9, 26.1, 17.8, 11.8. EIMS m/z488 (M+Na$^+$).

EXAMPLE 6c

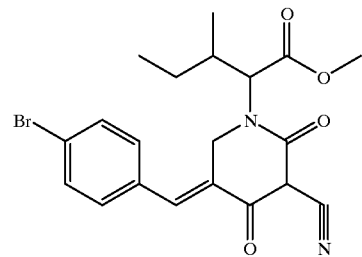

Preparation of and Data for 5-(E)-(2-(4-Bromophenyl)ethylene)-3-cyano-2,4-dioxo-N-(methoxycarbonyl(2-(methyl)propyl)methyl) piperidine The compound prepared in Example 6b (37 mg, 0.080 mmol) in THF (4 mL) was cooled down to about −78° C. Potassium tert-butoxide (1.0 M solution in 2-methyl-2-propanol) (0.3 mL, 0.3 mmol) was added. The mixture was stirred for about 3 h at about −78° C. The reaction mixture was quenched by saturated NH$_4$Cl solution (5 mL). The organic layer was removed. The aqueous layer was extracted by EtOAc (2×10 mL). The combined organic layers were washed by saturated NaCl solution (20 mL), dried over Na$_2$SO$_4$ and concentrated. Chromatography (CH$_2$Cl$_2$/MeOH) of the crude yellow oil afforded 23 mg (60%) of the title compound. $^1$H NMR (Pyridine-d$_5$, 500 MHz) δ 7.83 (s, 1H), 7.61–7.57 (two d, 4H, J=8.6 Hz), 5.14–5.11 (d, 1H, J=14.8 Hz), 4.47–4.44 (d, 1H, J=14.8 Hz), 4.32–4.30 (m, 2H), 3.89 (d, 1H, J=2.5 Hz), 3.71 (s, 3H), 1.92–1.75 (m, 3H), 0.91–0.85 (m, 6H). $^{13}$C NMR (CD$_3$OD, 500 MHz) δ 195.4, 176.6, 169.6, 167.6, 141.7, 135.1, 132.9, 132.7, 130.9, 124.3, 92.7, 66.3, 59.3, 52.9 (2C), 37.1, 36.6, 26.2, 13.4, 12.9. EIMS m/z 433 (M+H$^+$), 455 (M+Na$^+$).

EXAMPLE 7

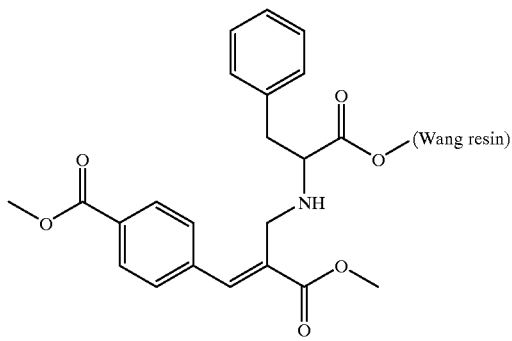

Attachment of Methyl 2-(Z)-(Bromomethyl)-3-(4-methoxycarbonyl-phenyl)prop-2-enoate to Fmoc-Phe-Wang Resin To Fmoc-Phe-Wang Resin (Novabiochem, 0.40 mmol/g) (1 g, 0.40 mmol) was added a solution containing 5 mL each of DMF and piperidine at about room temperature. The suspension was allowed to mix at about room temperature for about 2 h. The supernatant was then removed. The resin was washed with DMF, MeOH, CH$_2$Cl$_2$ and dried in vacuo. To the dyed resin were added the methyl 2-(Z)-(Bromomethyl)-3-(4-methoxycarbonylphenyl)prop-2-enoate (125 g, 0.40 mmol) prepared in Example 2b, Pd(PPh$_3$)$_4$ (4.6 mg, 0.004 mmol), Cs$_2$CO$_3$ (130 mg, 0.40 mmol) and DMF (10 mL) at about room temperature. The suspension was allowed to mix at about room temperature for about 16 h. After about 6 h, the supernatant was removed. The resin was washed with DMF, MeOH and CH$_2$Cl$_2$ and then dried in vacuo.

EXAMPLE 7a

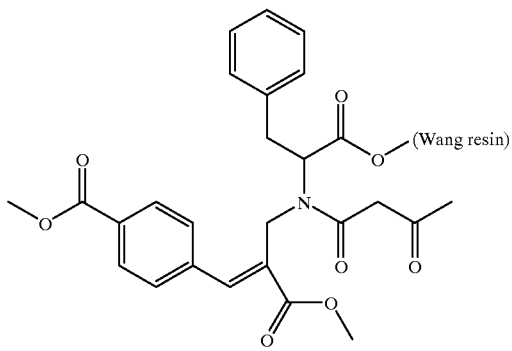

Attachment of Diketene to the Alkylated Fmoc-Phe-Wang Resin

A mixture of the resin prepared in Example 7 and Et$_3$N (0.6 μL, 0.004 mmol) in CH$_2$Cl$_2$ (10 mL) was stirred at about 0° C. Diketene (62 μL, 0.8 mmol) was added. The suspension was stirred for about 50 h at about 25° C. before the supernatant was removed. The resin was washed with MeOH, CH$_2$Cl$_2$ and dried in vacuo.

EXAMPLE 7b

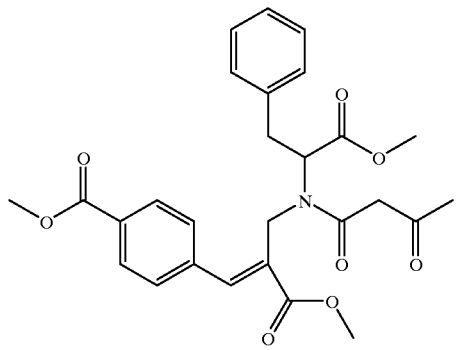

Preparation of and Data for Methyl (E)-N-(1,3-Dioxobutyl)-N-(2-methoxycarbonyl-3-(4-methoxycarbonylphenyl)prop-2-enyl)-2-amino-2-phenylpropionate To the resin prepared in Example 7a, TFA (10 mL) was added. The suspension was stirred for about 2 h at about 25° C. The supernatant was then removed and the resin was washed with MeOH (3×8 mL). The combined supernatants were concentrated and dried in vacuo. The residue was dissolved again in MeOH (10 mL) and (trimethylsilyl)diazomethane (2.0 M solution in hexanes) was added dropwise until the yellow color stayed. After concentration, chromatography (EtOAc/hexane) of the crude yellow oil afforded 57 mg of the title compound (total yield of about 29% from Example 7 to Example 7b). $^1$H NMR (CD$_3$OD, 500 MHz) δ 8.00–7.98 (d, 2H, J=8.0), 7.87 (s, 1H,), 7.20–7.17 (d, 2H, J=8.0), 7.05–6.72 (m, 5H), 4.37–4.34 (d, 1H, J=15.4), 3.99 (s, 3H), 3.83 (s, 3H), 3.90–3.60 (m, 2H), 3.61 (s, 3H), 3.53–3.50 (d, 1H, J=15.4), 3.47–3.43 (dd, 1H, J=4.6, 9.9 Hz), 3.05 (m, 2H), 2.24 (s, 3H). $^{13}$C NMR (CD$_3$OD, 500 MHz) δ 204.9, 171.8, 170.3, 168.3, 168.1, 143.9, 140.1, 138.9, 131.8, 131.2, 131.1, 130.8, 130.6, 129.6, 127.5, 62.2, 53.1, 52.9, 52.8 (2C), 47.2, 35.2, 30.7. EIMS m/z 496 (M+H$^+$), 518 (M+Na$^+$).

EXAMPLE 7c

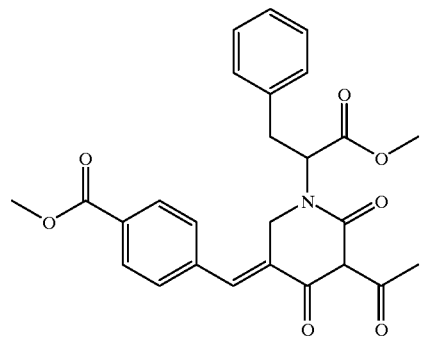

Preparation of and Data for 3-(E)-Acetyl-2,4-dioxo-N-(methoxycarbonyl(benzyl)methyl)-5-(2-(4-methoxycarbonylphenyl)-ethylene)piperidine The compound prepared in Example 7b (30 mg, 0.060 mmol) in THF (5 mL) was cooled down to about −78° C. Potassium tert-butoxide (1.0 M solution in 2-methyl-2-propanol) (0.2 mL, 0.2 mmol) was added. The mixture was stirred for about 3 h at about −78° C. The reaction mixture was quenched by saturated NH$_4$Cl solution (10 mL). The organic layer was removed. The aqueous layer was extracted by EtOAc (2×10 mL). The combined organic layers were washed by saturated NaCl solution (20 mL), dried over Na$_2$SO$_4$ and concentrated. Chromatography (CH$_2$Cl$_2$/MeOH) of the crude yellow oil afforded 18 mg (65% yield) of the title compound. $^1$H NMR (CD$_3$OD, 500 MHz) δ 8.03 (broad, 2H), 7.92 (s, 1H,), 7.70 (broad, 2H), 7.40–7.00 (broad, 5H), 5.10 (broad, 1H), 4.50 (broad d, 1H), 4.21 (broad, 1H), 3.84 (s, 3H), 3.74 (s, 3H), 3.50 (broad, 1H), 3.10 (broad, 1H), 2.80 (s, 3H). $^{13}$C NMR (CD$_3$OD, 500 MHz) δ. EIMS m/z 464 (M+H$^+$).

We claim:

1. A compound selected from those of the formula:

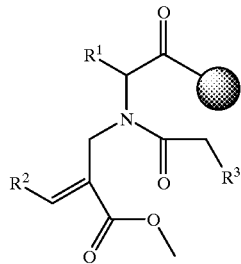

wherein:
- ◉ is a solid support;
- R$_1$ is selected from the group consisting of a standard natural amino acid side chain, CH$_3$, CFI(CH$_3$)CH$_2$CH$_3$ and CH$_2$Ph;
- R$_2$ is selected from the group consisting of alkyl, aralkyl, phenyl and substituted phenyl; where the substituents on the substituted phenyl group are selected from lower alkyl, halo, alkoxy, nitrile, cyano, alkoxycarbonyl, aryloxycarbonyl, nitro, furyl and substituted furyl; where the substituents on the substituted furyl group are selected from alkyl, halo, alkoxy, alkoxycarbonyl, nitrile, aryloxycarbonyl, nitro, thienyl and substituted thienyl; where the substituents on the substituted thienyl group are selected from lower alkyl, halo, alkoxy, nitrile, alkoxycarbonyl, aryloxycarbonyl, naphthyl and substituted naphthyl; where the substituents on the substituted naphthyl group are selected from lower alkyl, halo, alkoxy, nitrile, alkoxycarbonyl and aryloxycarbonyl; and,
- R$_3$ is selected from the group consisting of COOalkyl, CN, COloweralkyl, COaralkyl wherein said aralkyl is benzyl or substituted benzyl, and COaryl; where aryl is phenyl, substituted phenyl, thienyl, furyl or naphthyl.

2. A compound selected from those of the formula:

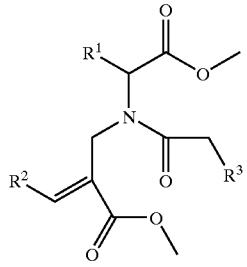

wherein:
- R$_1$ is selected from the group consisting of a standard natural amino acid side chain, CH$_3$, CH(CH$_3$)CH$_2$CH$_2$ and CH$_2$Ph;
- R$_2$ is selected from the group consisting of alkyl, aralkyl, phenyl and substituted phenyl; where the substituents on the substituted phenyl group are selected from lower alkyl, halo, alkoxy, nitrile, cyano, alkoxycarbonyl, aryloxycarbonyl, nitro, furyl and substituted furyl; where the substituents on the substituted furyl group are selected from alkyl, halo, alkoxy, alkoxycarbonyl, nitrile, aryloxycarbonyl, nitro, thienyl and substituted thienyl; where the substituents on the substituted thienyl group are selected from lower alkyl, halo, alkoxy, nitrile, alkoxycarbonyl, aryloxycarbonyl, naphthyl and substituted naphthyl; where the substituents on the substituted naphthyl group are selected from lower alkyl, halo, alkoxy, nitrile, alkoxycarbonyl and aryloxycarbonyl; and,
- R$_3$ is selected from the group consisting of COOalkyl, CN COloweralkyl, COaralkyl wherein said aralkyl is benzyl or substituted benzyl, and COaryl; where aryl is phenyl, substituted phenyl, thienyl, furyl or naphthyl.

3. A compound according to claim 1 of the formula:

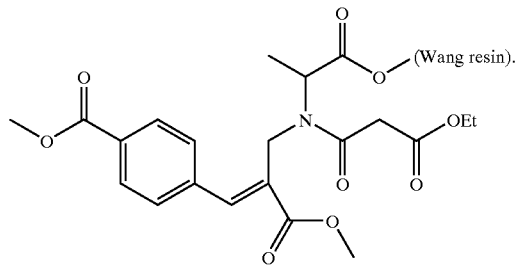

4. A compound according claim 2 of formula:

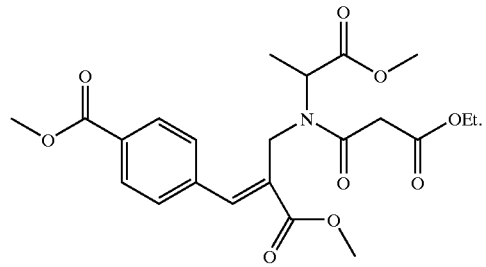

5. A compound according to claim 1 of the formula:

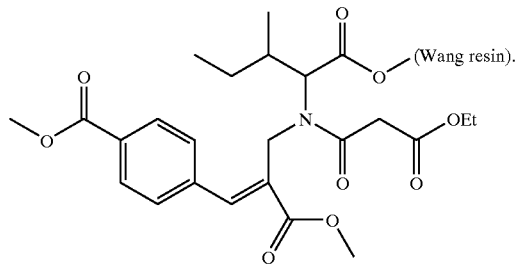

6. A compound according to claim 2 of the formula:

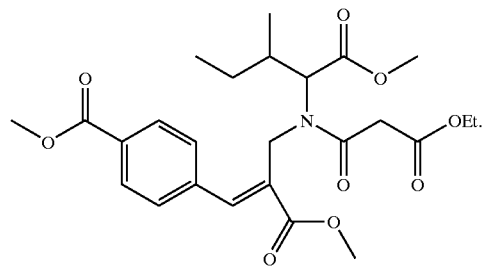

7. A compound according to claim 1 of the formula:
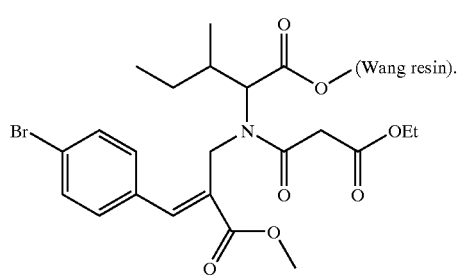
8. A compound according to claim 2 of the formula:
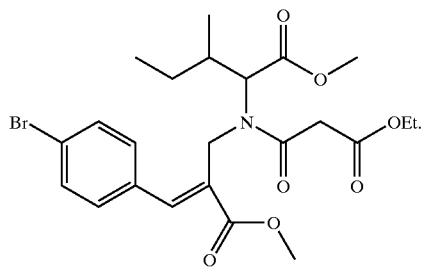
9. A compound according to claim 1 of the formula:
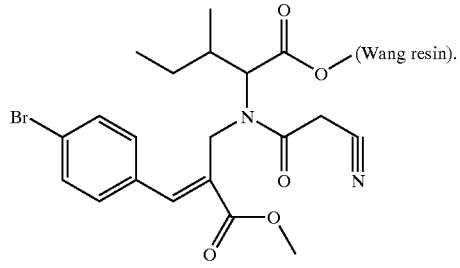
10. A compound according to claim 2 of the formula:
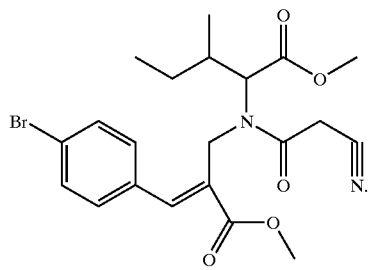
11. A compound according to claim 1 of the formula:
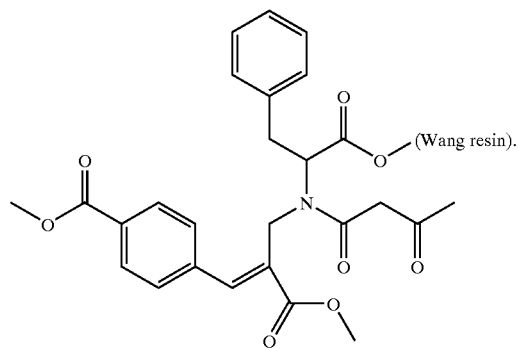
12. A compound according to claim 2 of the formula:
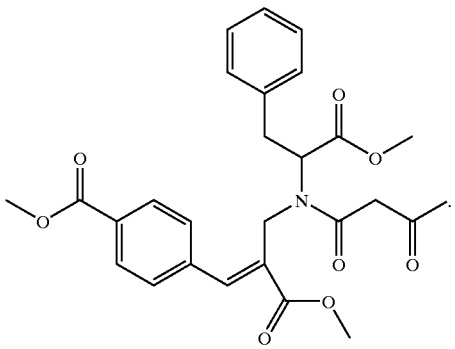
* * * * *

UNITED STATES PATENT AND TRADEMARK OFFICE
CERTIFICATE OF CORRECTION

PATENT NO.    : 6,686,503 B2
DATED         : February 3, 2003
INVENTOR(S)   : Chai Wenying and William V. Murray It is certified that error appears in the above-identified patent and that said Letters Patent is hereby corrected as shown below:

Column 21,
Line 26, second instance, please delete "CFI" and insert therefore -- CH --

Signed and Sealed this

Twenty-second Day of June, 2004

JON W. DUDAS
*Acting Director of the United States Patent and Trademark Office*